United States Patent
Hong et al.

(10) Patent No.: US 8,933,237 B2
(45) Date of Patent: Jan. 13, 2015

(54) METHODS FOR THE SYNTHESIS OF DEUTERATED VINYL PYRIDINE MONOMERS

(71) Applicant: UT-Battelle, LLC, Oak Ridge, TN (US)

(72) Inventors: Kunlun Hong, Knoxville, TN (US); Jun Yang, Oak Ridge, TN (US); Peter V. Bonnesen, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 14/156,916

(22) Filed: Jan. 16, 2014

(65) Prior Publication Data

US 2014/0213793 A1   Jul. 31, 2014

Related U.S. Application Data

(62) Division of application No. 13/553,293, filed on Jul. 19, 2012, now Pat. No. 8,658,802.

(51) Int. Cl.
  *C07D 213/06* (2006.01)
  *C07D 213/16* (2006.01)
  *C07D 213/127* (2006.01)

(52) U.S. Cl.
  CPC .......... *C07D 213/16* (2013.01); *C07D 213/127* (2013.01)
  USPC ...................................................... 546/352

(58) Field of Classification Search
  None
  See application file for complete search history.

(56) References Cited

U.S. PATENT DOCUMENTS 4,266,061 A    5/1981  Bönnemann et al.
2005/0148021 A1  7/2005  Pier

FOREIGN PATENT DOCUMENTS

JP     2010-64011     3/2010

OTHER PUBLICATIONS

Matsuzaki K. et al., "Stereoregularity of Poly(2-Vinylpyridine) Determined by $^1$H-NMR and $^{13}$C-NMR Spectroscopy", *Journal of Polymer Science: Polymer Chemistry Edition* 14:1475-1484 (1976).
Matsuzaki K. et al., "Stereoregularity of Poly(2-Vinylpyridine) and Poly-(4-Vinylpyridine)", *Journal of Polymer Science: Polymer Chemistry Edition* 15:1573-1583 (1977).
Matsuzaki K. et al., "NMR Spectra of Poly-2-Vinylpyridine", *Journal of Polymer Science* Part A-2, vol. 5, pp. 1320-1322 (1967).
Sebastiano R. et al., "A New Deuterated Alkylating Agent for Quantitative Proteomics", *Rapid Communications in Mass Spectrometry* 17:2380-2386 (2003).
Esaki H. et al., "General Method of Obtaining Deuterium-Labeled Heterocyclic Compounds Using Neutral $D_2O$ with Heterogeneous Pd/C", *Tetrahedron* 62:10954-10961 (2006).
Ito N. et al., "Efficient and Selective Pt/C-Catalyzed H-D Exchange Reaction of Aromatic Rings", *Bull. Chem. Soc. Jpn.* 81(2):278-286 (2008).
Ito N. et al., "Bimetallic Palladium—Platinum-on-Carbon-Catalyzed H-D Exchange Reaction: Synergistic Effect on Multiple Deuterium Incorporation", *Synthesis* 16:2674-2678 (2009).
Tse S.K.S. et al., "Hydrogen/Deuterium Exchange Reactions of Olefins with Deuterium Oxide Mediated by the Carbonylchlorohydrido-Tris (Triphenylphosphine)Ruthenium(II) Complex", *Adv. Synth. Catal.* 352:1512-1522 (2010).
Cho B.T. et al., "Solvent-Free Reduction of Aldehydes and Ketones Using Solid Acid-Activated Sodium Borohydride", *Tetrahedron* 62:8164-8168 (2006).
Jenkins W.L. et al., "Oligomerization Stereochemistry of Vinyl Monomers. IV. Ion-Pair Structure and β-Carbon Stereochemistry in Anionic Oligomerization of 2-Vinylpyridine", *Journal of Polymer Science: Polymer Letters Edition* 16:501-506 (1978).
Wang H-T et al., "$^1$H-NMR Spectra of Epimerized Polymers Derived from Isotactic Polyβ,β-Dideuterio-2-Vinylpyridine)", *Eur. Polym. J.* 29(2/3):401-406 (1993).
Hogen-Esch T.E. et al., "Oligomerization Stereochemistry of Vinyl Monomers. 8. β-Carbon Stereochemistry and Carbanion Structure in the Oligomerization of 2- and 4-Vinylpyridines", *Macromolecules* 14:510-516 (1981).
Righetti P.G. et al., "Isotope-Coded Two-Dimensional Maps: Tagging with Deuterated Acrylamide and 2-Vinylpyridine", *Methods in Molecular Biology*, vol. 424:*2D PAGE: Sample Preparation and Fractionation*, vol. 1, Humana Press (2008).
Spiegel M.J. et al., "The Reduction of the Acetylpyridine Analogue of Diphosphopyridine Nucleotide by Dihydro-diphosphopyridine Nucleotide", *The Journal of Biological Chemistry* 235(8):2498-2501 (Aug. 1960).
Kutney J.P. et al., "Synthesis in the Pyridine Series, III. The Synthesis of New 3,5-Dimethyl-4-Substituted Pyridines. Steric Effects as an Aid to Synthesis", *Canadian Journal of Chemistry* 41:695-702 (1963).

*Primary Examiner* — Zinna Northington Davis
(74) *Attorney, Agent, or Firm* — Scully, Scott, Murphy & Presser, P.C.

(57) ABSTRACT

Methods for synthesizing deuterated vinylpyridine compounds of the Formula (1), wherein the method includes: (i) deuterating an acyl pyridine of the Formula (2) in the presence of a metal catalyst and $D_2O$, wherein the metal catalyst is active for hydrogen exchange in water, to produce a deuterated acyl compound of Formula (3); (ii) reducing the compound of Formula (3) with a deuterated reducing agent to convert the acyl group to an alcohol group, and (iii) dehydrating the compound produced in step (ii) with a dehydrating agent to afford the vinylpyridine compound of Formula (1). The resulting deuterated vinylpyridine compounds are also described.

28 Claims, No Drawings

METHODS FOR THE SYNTHESIS OF DEUTERATED VINYL PYRIDINE MONOMERS

CROSS REFERENCE TO RELATED APPLICATIONS

This application is a divisional of U.S. application Ser. No. 13/553,293 filed on Jul. 19, 2012, now U.S. Pat. No. 8,658,802 the contents of which are incorporated herein by reference in their entirety.

This invention was made with government support under Prime Contract No. DE-AC05-00OR22725 awarded by the U.S. Department of Energy. The government has certain rights in the invention.

FIELD OF THE INVENTION

The present invention relates, generally, to polymerizable deuterated monomers and methods of preparation, and more particularly, to deuterated and partially deuterated vinyl pyridine monomers and methods of preparation.

BACKGROUND OF THE INVENTION

Deuterated polymers are well-recognized for their use in the elucidation of structure-property relationships in a variety of materials, such as in amphiphilic polymers or in proteins (e.g., in proteomic analysis). Deuterated polymers have also found use in elucidating surface adsorption mechanisms and properties of their non-deuterated counterparts. Neutron scattering techniques, such as small angle neutron scattering (SANS), are among the more common techniques used for studying deuterated polymers.

Polyvinylpyridines, in particular, are used in a variety of applications, including as conductive polymers (e.g., as produced from polyvinylpyridine and iodine) used as battery cathode materials, photographic materials, textiles, dispersing agents, and ion exchange materials. Therefore, to further elucidate the properties and interactive behavior of the polyvinylpyridines on a molecular level, deuterated forms of polyvinylpyridines and methods of producing them continue to be sought.

A possible route for making a deuterated polyvinylpyridine is by polymerizing a deuterated vinylpyridine (monomer). However, a significant drawback in current methods for producing deuterated vinylpyridines is their inability to provide specific levels of deuteration and selected deuteration patterns, particularly on the pyridine ring. In particular, current methods are generally incapable of providing partial deuteration of the pyridine ring. Yet, partial deuteration of the pyridine ring would be particularly advantageous for optimizing the scattering length density (SLD) in devising certain neutron scattering experiments where partially deuterated polymers are used to match the background, or to decouple the intra- and inter-structural and dynamic information.

SUMMARY OF THE INVENTION

The invention is directed to a method for the preparation of deuterated vinylpyridine compounds. The invention is also directed to deuterated vinylpyridine compounds produced by the method, as well as deuterated polyvinylpyridine polymers produced therefrom.

The invention is particularly directed to a method for the synthesis of deuterated vinylpyridine compounds of the formula:

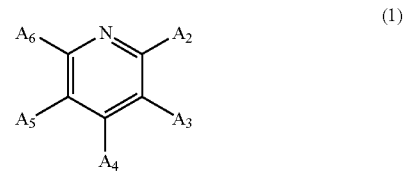

wherein one of $A_2$, $A_3$, $A_4$, $A_5$, and $A_6$ is a vinyl group of the formula:

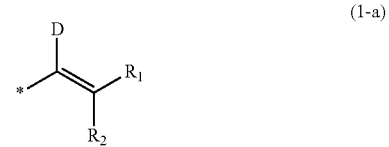

wherein $R_1$ and $R_2$ are each independently either a deuterium atom or a perdeuterated alkyl group containing one to six carbon atoms, and the remainder of $A_2$, $A_3$, $A_4$, $A_5$, and $A_6$ are independently selected from hydrogen and deuterium atoms.

The method includes a first step of deuteration of an acyl (e.g., acetyl) pyridine, as follows:

(i) deuterating a compound of Formula (2) to a compound of Formula (3) by the following reaction pathway conducted in the presence of a metal catalyst and $D_2O$, wherein the metal catalyst is active for hydrogen exchange in water:

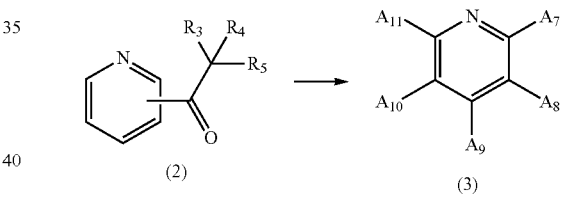

$R_3$, $R_4$, and $R_5$ are independently selected from hydrogen atom and alkyl groups containing one to six carbon atoms, provided that at least one of $R_3$, $R_4$, and $R_5$ is a hydrogen atom;

one of $A_7$, $A_8$, $A_9$, $A_{10}$, and $A_{11}$ is an acyl group of the formula:

wherein $R_6$, $R_7$, and $R_8$ are independently selected from deuterium atom and perdeuteroalkyl groups containing one to six carbon atoms, provided that at least one of $R_6$, $R_7$, and $R_8$ is a deuterium atom.

The method includes a second step of reducing the deuterated product of step (i), as follows:

(ii) reducing the compound of Formula (3) with a deuterated reducing agent to convert the acyl group of Formula (3-a) to an alcohol group of the Formula (3-b):

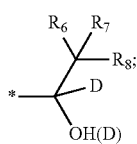

(3-b)

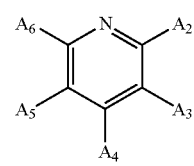

(1)

The method includes a third step of dehydrating the compound produced in step (ii) with a dehydrating agent to afford the vinylpyridine compound of Formula (1).

The method may also include an additional step wherein a vinylpyridine compound of Formula (1) is reacted with a Bronsted acid (e.g., HBr or HI) or alkylating agent (e.g., methyl bromide or methyl iodide) to produce a charged pyridinium species wherein the nitrogen atom of the pyridine ring is bound to a hydrogen atom, deuterium atom, or an alkyl group optionally substituted with one or more deuterium atoms. In such a case, the Bronsted acid is optionally deuterated, and the alkylating agent contains an alkyl group optionally substituted with one or more deuterium atoms. Thus, Formula (1) encompasses neutral pyridine and charged pyridinium compounds.

By judicious selection of reaction conditions, particularly of step (i), the method described above can produce vinylpyridine compounds having a specific level of deuteration or a selected deuteration pattern, particularly on the pyridine ring. Some of the reaction conditions of particular importance in providing the selective deuteration include the type of metal catalyst, the temperature, the pressure, and the vinylpyridine isomer used in step (i). In a first set of embodiments, the vinyl moiety is completely deuterated (for example, with three deuterium atoms) while the pyridine moiety is non-deuterated. In a second set of embodiments, the vinyl moiety is completely deuterated and the pyridine moiety is also completely deuterated (i.e., with four deuterium atoms). In a third set of embodiments, the vinyl moiety is completely deuterated while the pyridine moiety is partially deuterated, such as with one, two, or three deuterium atoms. In the case of partial deuteration of the pyridine moiety, the partial deuteration may also provide for deuteration at specific locations on the pyridine ring.

Moreover, the method described above can advantageously produce a completely deuterated vinylpyridine compound in significant yields in a highly cost-effective and straight-forward manner. The method is also advantageously amenable to significant scale up. Thus, the method can advantageously make such deuterated vinylpyridine compounds substantially more available for a variety of applications.

In other aspects, the invention is directed to methods of using the deuterated vinylpyridine compounds for the synthesis of deuterated polyvinylpyridine polymers and copolymers. The invention is also directed to methods of using the deuterated polyvinylpyridine polymers in any of a variety of applications, such as battery cathode materials, photographic materials, textiles, dispersing agents, and ion exchange materials.

DETAILED DESCRIPTION OF THE INVENTION

The deuterated vinylpyridine compounds considered herein have the following formula:

In Formula (1), one of $A_2$, $A_3$, $A_4$, $A_5$, and $A_6$ is a vinyl group of the formula:

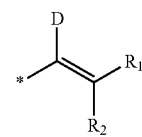

(1-a)

In Formula (1-a), $R_1$ and $R_2$ are each independently either a deuterium atom (D) or a perdeuterated alkyl group containing one to six carbon atoms. The perdeuterated alkyl group can be straight-chained or branched, and may contain one, two, three, four, five, or six carbon atoms, or a number of carbon atoms within a range thereof. Some examples of perdeuterated alkyl groups include trideuteromethyl, pentadeuteroethyl, heptadeuteropropyl, heptadeuteroisopropyl, perdeuterobutyl, perdeuteropentyl, and perdeuterohexyl groups.

In one set of embodiments, $R_1$ and $R_2$ are both deuterium atoms. In another set of embodiments, one of $R_1$ and $R_2$ is a deuterium atom and another of $R_1$ and $R_2$ is a perdeuterated alkyl group. In another set of embodiments, $R_1$ and $R_2$ are both perdeuterated alkyl groups, which may have the same or a different number of carbon atoms.

The remainder (i.e., aside from the vinyl group of Formula 1-a) of $A_2$, $A_3$, $A_4$, $A_5$, and $A_6$ are independently selected from hydrogen and deuterium atoms. In some embodiments, at least one, two, or three of $A_2$, $A_3$, $A_4$, $A_5$, and $A_6$ are hydrogen atoms (i.e., not all of $A_2$, $A_3$, $A_4$, $A_5$, and $A_6$ are deuterium atoms), while in other embodiments, at least one, two, or three of $A_2$, $A_3$, $A_4$, $A_5$, and $A_6$ are deuterium atoms (i.e., not all of $A_2$, $A_3$, $A_4$, $A_5$, and $A_6$ are hydrogen atoms). In a first set of embodiments, the remainder of $A_2$, $A_3$, $A_4$, $A_5$, and $A_6$ are all hydrogen atoms. In a second set of embodiments, one of $A_2$, $A_3$, $A_4$, $A_5$, and $A_6$ is a deuterium atom, with the remainder being hydrogen atoms. In a third set of embodiments, two of $A_2$, $A_3$, $A_4$, $A_5$, and $A_6$ are deuterium atoms, with the remainder being hydrogen atoms. The two deuterium atoms can be, for example, $A_2$ and $A_3$, or $A_2$ and $A_4$, or $A_2$ and $A_5$, or $A_2$ and $A_6$, or $A_3$ and $A_4$, or $A_3$ and $A_5$, or $A_3$ and $A_6$, or $A_4$ and $A_5$, or $A_4$ and $A_6$, or $A_5$ and $A_6$. In a fourth set of embodiments, three of $A_2$, $A_3$, $A_4$, $A_5$, and $A_6$ are deuterium atoms, with the remainder being a hydrogen atom. The three deuterium atoms can be, for example, $A_2$, $A_3$, and $A_4$, or $A_2$, $A_3$, and $A_5$, or $A_2$, $A_3$, and $A_6$, or $A_2$, $A_4$, and $A_5$, or $A_2$, $A_4$, and $A_6$, or $A_2$, $A_5$, and $A_6$, or $A_3$, $A_4$, and $A_5$, or $A_3$, $A_4$, and $A_6$, or $A_3$, $A_5$, and $A_6$, or $A_4$, $A_5$, and $A_6$. In a fifth set of embodiments, the remainder of $A_2$, $A_3$, $A_4$, $A_5$, and $A_6$ are all deuterium atoms.

In a first set of embodiments, $A_2$ or $A_6$ is the vinyl group of Formula (1-a), which results in a vinylpyridine compound having the following structure:

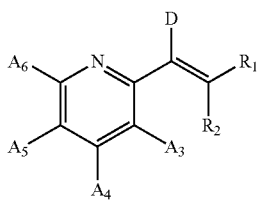

(1-1)

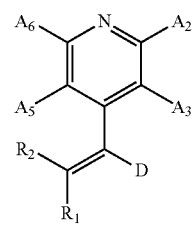

(1-3)

In particular embodiments of Formula (1-1), $R_1$ and $R_2$ are both deuterium atoms. In one set of embodiments thereof, all of $A_3$, $A_4$, $A_5$, and $A_6$ are hydrogen atoms. In another set of embodiments, one of $A_3$, $A_4$, $A_5$, and $A_6$ is a deuterium atom with the remainder being hydrogen atoms. In another set of embodiments, two of $A_3$, $A_4$, $A_5$, and $A_6$ are deuterium atoms with the remainder being hydrogen atoms. The two deuterium atoms can be, for example, $A_3$ and $A_4$, or $A_3$ and $A_5$, or $A_3$ and $A_6$, or $A_4$ and $A_5$, or $A_4$ and $A_6$, or $A_5$ and $A_6$. In another set of embodiments, three of $A_3$, $A_4$, $A_5$, and $A_6$ are deuterium atoms with the remainder being hydrogen atoms. The three deuterium atoms can be, for example, $A_3$, $A_4$, and $A_5$, or $A_3$, $A_4$, and $A_6$, or $A_3$, $A_5$, and $A_6$, or $A_4$, $A_5$, and $A_6$. In yet another set of embodiments, all of $A_3$, $A_4$, $A_5$, and $A_6$ are deuterium atoms.

In a second set of embodiments, $A_3$ or $A_5$ is the vinyl group of Formula (1-a), which results in a vinylpyridine compound having the following structure:.

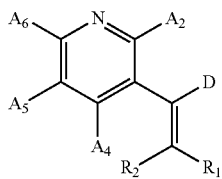

(1-2)

In particular embodiments of Formula (1-2), $R_1$ and $R_2$ are both deuterium atoms. In one set of embodiments thereof, all of $A_2$, $A_4$, $A_5$, and $A_6$ are hydrogen atoms. In another set of embodiments, one of $A_2$, $A_4$, $A_5$, and $A_6$ is a deuterium atom with the remainder being hydrogen atoms. In another set of embodiments, two of $A_2$, $A_4$, $A_5$, and $A_6$ are deuterium atoms with the remainder being hydrogen atoms. The two deuterium atoms can be, for example, $A_2$ and $A_4$, or $A_2$ and $A_5$, or $A_2$ and $A_6$, or $A_4$ and $A_5$, or $A_4$ and $A_6$, or $A_5$ and $A_6$. In another set of embodiments, three of $A_2$, $A_4$, $A_5$, and $A_6$ are deuterium atoms with the remainder being hydrogen atoms. The three deuterium atoms can be, for example, $A_2$, $A_4$, and $A_5$, or $A_2$, $A_4$, and $A_6$, or $A_2$, $A_5$, and $A_6$, or $A_4$, $A_5$, and $A_6$. In yet another set of embodiments, all of $A_2$, $A_4$, $A_5$, and $A_6$ are deuterium atoms.

In a third set of embodiments, $A_4$ is the vinyl group of Formula (1-a), which results in a vinylpyridine compound having the following structure:

In particular embodiments of Formula (1-3), $R_1$ and $R_2$ are both deuterium atoms. In one set of embodiments thereof, all of $A_2$, $A_3$, $A_5$, and $A_6$ are hydrogen atoms. In another set of embodiments, one of $A_2$, $A_3$, $A_5$, and $A_6$ is a deuterium atom with the remainder being hydrogen atoms. In another set of embodiments, two of $A_2$, $A_3$, $A_5$, and $A_6$ are deuterium atoms with the remainder being hydrogen atoms. The two deuterium atoms can be, for example, $A_2$ and $A_3$, or $A_2$ and $A_5$, or $A_2$ and $A_6$, or $A_3$ and $A_5$, or $A_3$ and $A_6$, or $A_5$ and $A_6$. In another set of embodiments, three of $A_2$, $A_3$, $A_5$, and $A_6$ are deuterium atoms with the remainder being hydrogen atoms. The three deuterium atoms can be, for example, $A_2$, $A_3$, and $A_5$, or $A_2$, $A_3$, and $A_6$, or $A_2$, $A_5$, and $A_6$, or $A_3$, $A_5$, and $A_6$. In yet another set of embodiments, all of $A_2$, $A_3$, $A_5$, and $A_6$ are deuterium atoms.

Moreover, any of the above-described compounds according to Formula (1) may be excluded. For example, in some embodiments, when $A_2$, $A_4$, or $A_6$ is the vinyl group of Formula (1-a), and $R_1$ and $R_2$ are both deuterium atoms, then the remainder of $A_2$, $A_3$, $A_4$, $A_5$, and $A_6$ are not all hydrogen atoms. In other embodiments, when $A_2$ or $A_6$ is the vinyl group of Formula (1-a) and $R_1$ and $R_2$ are both deuterium atoms, then the remainder of $A_2$, $A_3$, $A_4$, $A_5$, and $A_6$ are not all deuterium atoms. In yet other embodiments, when $A_4$ is the vinyl group of Formula (1-a), and $R_1$ and $R_2$ are both deuterium atoms, then $A_2$, $A_3$, $A_5$, and $A_6$ are not all deuterium atoms.

The structure shown in Formula (1) may also include positively charged pyridinium species wherein the nitrogen atom of the pyridine ring is bound to a hydrogen atom, a deuterium atom, or an alkyl group (e.g., as described above, having one to six carbon atoms) optionally substituted with one or more deuterium atoms. Thus, Formula (1) also includes one or more counteranions associated with the pyridinium cation. The counteranion can be, for example, a halide (e.g., chloride, bromide, iodide), acetate, sulfate, sulfonate, phosphate, phosphonate, nitrate, methylsulfonate, trifluormethylsulfonate, tetrafluoroborate, borate, or boronate.

The method described herein for synthesizing a compound according to Formula (1) includes at least steps (i)-(iii), as further described below.

The first step, i.e., step (i), includes deuterating a compound of Formula (2) to a compound of Formula (3) by the following reaction pathway conducted in the presence of a metal catalyst and deuterated water ($D_2O$), wherein the metal catalyst is active for hydrogen exchange in water:

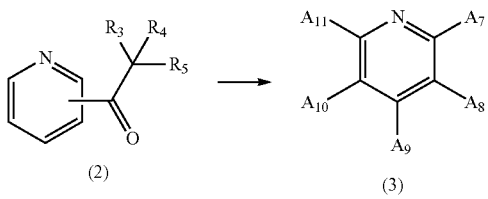

In Formula (2) above, $R_3$, $R_4$, and $R_5$ are independently selected from hydrogen atom and alkyl groups containing one to six carbon atoms, provided that at least one of $R_3$, $R_4$, and $R_5$ is a hydrogen atom. The alkyl groups containing one to six carbon atoms can be straight-chained or branched. Some examples of such alkyl groups include methyl, ethyl, n-propyl, isopropyl, n-butyl, isobutyl, sec-butyl, tert-butyl, n-pentyl, isopentyl, neopentyl, n-hexyl, and isohexyl groups. In a particular embodiment, $R_3$, $R_4$, and $R_5$ are all hydrogen atoms. In other embodiments, one or two of $R_3$, $R_4$, and $R_5$ are alkyl groups.

In Formula (3), one of $A_7$, $A_8$, $A_9$, $A_{10}$, and $A_{11}$ is an acyl group of the formula:

wherein $R_6$, $R_7$, and $R_8$ are independently selected from deuterium atom and perdeuteroalkyl groups containing one to six carbon atoms, as described above, provided that at least one of $R_6$, $R_7$, and $R_8$ is a deuterium atom. In a particular embodiment, $R_6$, $R_7$, and $R_8$ are all deuterium atoms, which results when $R_3$, $R_4$, and $R_5$ are all hydrogen atoms. In other embodiments, one or two of $R_6$, $R_7$, and $R_8$ are perdeuteroalkyl groups (with remaining group being D), which results when one or two of $R_3$, $R_4$, and $R_5$ are alkyl groups, respectively.

The metal catalyst involved in the transformation of step (i) includes at least one metal that is catalytically active for hydrogen exchange in water. The metal catalyst can be a homogeneous or heterogeneous catalyst, and may include a support, or be without a support, such as a soluble metal complex. Some examples of support materials include carbon, alumina, silica, calcium carbonate, calcium sulfate, barium sulfate, and zeolites. The metal can be loaded on the support in any suitable amount, such as 1 wt %, 2 wt %, 5 wt %, 10 wt %, 15 wt %, or 20 wt %. The metal of the metal catalyst may be a single metal or may be a combination of two or more metals, at least one of which is catalytically active for hydrogen exchange in water. Some examples of catalytic metals include the catalytically active transition metals, particularly the noble metals. Some particular examples of catalytically active noble metals include palladium, platinum, rhodium, and iridium. Gold and silver may also be used. Other catalytically active transition metals include iron, cobalt, nickel, molybdenum, ruthenium, rhenium, and tungsten. In some embodiments, the metal is in ionic form, while in other embodiments the metal is in the zerovalent state. In particular embodiments, a combination of catalytic metals is used, such as a combination of palladium and platinum. In some embodiments, a heterogeneous combination of catalysts is used, such as Pt/C in admixture with Pd/C, wherein the catalysts may be used in a relative ratio of, for example, 1:10, 1:5, 1:2, 1:1, 2:1, 5:1, or 10:1 (typically by weight), or within a range bounded by any two of these ratios. In other embodiments, each of the catalysts in an admixture of catalysts may be used in a relative amount of about, at least, above, up to, or less than, for example, 1%, 2%, 5%, 10%, 15%, 20%, 25%, 30%, 40%, 50%, 60%, 70%, 80%, 90%, 95%, 98%, or 99% by total weight of the catalysts in the admixture, wherein it is understood that the sum of the weight percents of the catalysts is 100%. Moreover, any one or more of the foregoing classes or specific types of catalytic metals may be excluded from the metal catalyst or entire process of step (i).

In some embodiments, the metal catalyst includes the metal as a metal-ligand complex. The ligand can be, for example, a monodentate, bidentate, tridentate, tetradentate, pentadentate, or hexadentate ligand. The ligand preferably does not function to poison the metal catalyst or in any other way inhibit or have a deleterious impact on the metal catalyst or other aspects of the reaction. Moreover, in some embodiments, the metal is bound to one type of ligand, whereas in other embodiments, the metal is bound to two or more different types of ligand. In one set of embodiments, the ligand is a halide, such a fluoride, chloride, bromide, or iodide ligand. In another set of embodiments, the ligand is an amine, such as amine ($NH_3$), a primary amine (e.g., an alkylamine, such as methylamine or isopropylamine), a secondary amine (e.g., a dialkylamine, such as diisopropylamine), or a tertiary amine (e.g., trimethylamine). The amine ligand can also be a diamine (e.g., ethylenediamine), triamine (e.g., diethylenetriamine), or higher multiple amine. The amine ligand may also be cyclic and either aromatic or aliphatic, such as pyridine or piperidine. In another set of embodiments, the ligand is a phosphine, such as trimethylphosphine, triethylphosphine, triphenylphosphine, or 1,2-bis(diphenylphosphino)ethane. In another set of embodiments, the ligand is a mercaptan, such as thiophenol, except that in some embodiments, mercaptans can be excluded if they function to inoperably or partially poison the metal catalyst. In another set of embodiments, the ligand is a carboxylate, such as acetate, propionate, butyrate, oxalate, or malonate. In another set of embodiments, the ligand is an unsaturated hydrocarbon group, such as cyclopentadienyl (Cp), pentamethylcyclopentadienyl (Cp*), cyclooctatetraene (COT), cyclooctadiene (COD), and vinylidene ligands. In another set of embodiments, the ligand is a diketo ligand, such as acetylacetonate (acac). The ligand may also be carbon monoxide (CO). Some particular examples of such metal catalysts include $[Cp^*IrCl_2]_2$, $NiCp(PPh_3)Cl$, $Ni(COD)_2$, $Pd(acac)_2$, and $Pt(acac)_2$. The metal catalyst may also be used in conjunction with a catalyst promoter, such as hydrogen gas.

The process of step (i) is generally conducted at a temperature above room temperature (i.e., where room temperature is generally considered about 20, 25, or 30° C.), and more typically, a temperature of precisely, about, at least, or above 50° C., 60° C., 70° C., 80° C., 90° C., 100° C., 110° C., 120° C., 130° C., 140° C., 150° C., 160° C., 170° C., 180° C., 190° C., 200° C., 210° C., 220° C., 230° C., 240° C., 250° C., 260° C., 270° C., 280° C., 290° C., 300° C., 310° C., 320° C., 330° C., 340° C., or 350° C., or a temperature within a range bounded by any two of the foregoing exemplary temperatures. The temperature is generally below the critical temperature of water, i.e., less than 374° C. In particular embodiments, the temperature is in the range of 130-230° C., or more particularly 140-220° C., or 150-210° C., or 160-200° C., or 170-190° C.

As used herein, the term "about" generally indicates within ±0.5%, 1%, 2%, 5%, or up to ±10% of the indicated value. For example, a temperature of about 25° C. generally indicates in its broadest sense 25° C.±10%, which indicates 22.5-27.5° C.

In some embodiments, the process of step (i) is conducted at standard atmospheric pressure, i.e., about 1 atm, or about 14.7 psi. In other embodiments, the process of step (i) is conducted at a pressure above 1 atm. In different embodiments, the pressure is precisely, about, at least, above, or up to, for example, 2, 3, 4, 5, 6, 7, 8, 9, 10, 15, 20, 30, 40, 50, 60, 70, 80, 90, 100, 125, 150, 175, or 200 atm, or a pressure within a range bounded by any two of the foregoing exemplary pressures. In other terms, the pressure can be precisely, about, at least, above, or up to, for example, 15, 20, 50, 70, 100, 120, 130, 140, 150, 160, 170, 180, 200, 250, 300, 350, 400, 450, 500, 550, 600, 700, 800, 900, 1000, 1500, 2000, 2500, or 3000 psi, or a pressure within a range bounded by any two of the foregoing exemplary pressures. The pressure is generally below the critical pressure of water, i.e., less than 218 atm (approximately 3200 psi). In particular embodiments, the pressure is in the range of 100-200 psi, or more particularly, 110-190 psi, or 120-180 psi, or 130-170 psi, or 140-160 psi.

The reaction of step (i) is generally maintained at a particular temperature (or within a range of temperatures) and a particular pressure (or within a range of pressures) set forth above for a suitable period of time (processing time) for the reaction to be completed. It is understood that higher temperatures generally require a shorter period of time to bring the reaction to completion. Depending on the conditions used (e.g., temperature, catalyst, pressure, and reactants being processed), the processing time can be anywhere from, for example, 0.5 to 72 hours. In different embodiments, depending on the conditions, the processing time is precisely, about, at least, above, or up to, for example, 0.5, 1, 2, 3, 4, 5, 10, 12, 15, 18, 20, 24, 30, 36, 40, 48, 56, 60, 68, or 72 hours, or a processing time within a range bounded by any of the foregoing exemplary processing times.

The product of step (i) may be separated from the reaction medium and purified according to any of the techniques well known in the art. For example, the product of step (i) may be filtered to remove the catalyst, the product in the filtrate extracted into an organic phase, the organic phase containing the product dried with a drying agent, and the volatile portion of the organic phase removed by evaporation to provide an initially isolated product of step (i) according to Formula (3). If desired, the initially isolated product of step (i) may be crystallized, recrystallized, or otherwise purified by techniques well known in the art. Alternatively, the product of step (i) is not separated or isolated from the reaction medium, except for removal of catalyst, before proceeding with step (ii), if the reducing agent used in step (ii) is compatible with water, or if other adjustments are made (e.g., addition of a pacifying solvent) to make the steps integratable.

The second step, i.e., step (ii), includes reducing the compound of Formula (3) in the presence of a deuterated reducing agent to convert the acyl group of Formula (3-a) to an alcohol group of the following Formula (3-b):

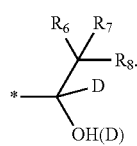

(3-b)

In Formula (3-b), $R_6$, $R_7$, and $R_8$ retain the same meanings provided above. The designation OH(D) indicates that the shown hydroxyl group may or may not be deuterated.

In step (ii), the deuterated reducing agent can be any deuterated reducing agent effective for this purpose. The deuterated reducing agent can be, for example, an aluminum deuteride (e.g., $LiAlD_4$ or lithium tri(t-butoxy)aluminodeuteride), a borodeuteride (e.g., $NaBD_4$, diborane-$d_6$, or sodium cyanoborodeuteride), or deuterium (i.e., $D_2$, along with appropriate catalyst).

As step (ii) is generally exothermic, the reaction is generally conducted without application of external heat. Generally, either the deuterated reducing agent is added to the compound of Formula (3) at a suitably slow rate, and/or the reaction is cooled. Typically, the reaction of step (ii) is conducted at standard pressure; however, an elevated pressure may be used, which may be any of the pressures described above for step (i). The product of step (ii) may be separated, isolated, or purified by any of the techniques known in the art, as described above for step (i).

The third step, i.e., step (iii), includes dehydrating the product of step (ii) with a dehydrating agent to afford the vinylpyridine compound of Formula (1). The dehydrating agent can be any dehydrating agent known in the art useful for converting an alcohol to an olefin, such as by acid-catalyzed dehydration, as well known in the art. Some examples of suitable dehydrating agents include sulfuric acid, phosphoric acid, the superacids (e.g., sulfonic acids, such as methanesulfonic acid), and alumina. Generally, the dehydration reaction is conducted either at room temperature or at an elevated temperature as provided for step (i).

The process for producing compounds of Formula (1) typically results in a series of compounds differing in the extent of deuteration or deuteration pattern on the pyridine ring. Of particular interest are those reaction conditions that exhibit a degree of selectivity by maximizing certain deuterated compounds while minimizing other deuterated compounds of Formula (1). The level of deuteration of the pyridine ring can be expressed as % D3 (non-deuterated pyridine ring with three D's on vinyl group), % D4 (one D on pyridine ring and three D's on vinyl group), % D5 (two D's on pyridine ring and three D's on vinyl group), % D6 (three D's on pyridine ring and three D's on vinyl group), and % D7 (completely deuterated pyridine ring with three D's on vinyl group). In different embodiments, a % D3, % D4, % D5, % D6, or a % D7 pyridine compound, or a combination of two or three of these, or any specific compound or combination of compounds described above, is produced in a relative amount of at least 50 mol %, 60 mol %, 65 mol %, 70 mol %, 75 mol %, 80 mol %, 85 mol %, 90 mol %, 95 mol %, or 97 mol % and up to about 100 mol %, or in an amount within a range bounded by any two of the foregoing values. Although vinylpyridine compounds having incomplete deuteration of the vinyl group (i.e., % D1 and % D2) are possible, the methods described herein generally produce these in minimal amounts, with % D 1 generally not detectable (i.e., effectively absent) and % D2 typically less than 3, 2, or 1 mol %.

In a first particular set of embodiments, at least or above 50, 60, 65, 70, 80, 85, 90, or 95 mol % of the compounds of Formula (1) has one of $A_2, A_3, A_4, A_5$, and $A_6$ as a vinyl group of the Formula (1-a) and two or three of $A_2, A_3, A_4, A_5$, and $A_6$ as deuterium atoms. In particular embodiments for achieving this, a mixed Pd/Pt catalyst is used in step (i). The mixed Pd/Pt catalyst can be any of the mixed Pd/Pt catalysts described above. Particularly when the process using mixed Pd/Pt catalyst is used on an ortho-acyl pyridine of Formula (2), i.e., when $A_2$ or $A_6$ is acyl, one or a combination of % D5 and % D6 vinylpyridine compounds of Formula (1) can be produced in an amount of at least or above 50, 60, 65, 70, 80, 85, 90, or 95 mol %, particularly with $A_4$, $A_5$, and/or $A_6$ as deuterium atoms in a predominant amount (with $A_2$ or $A_6$ acyl groups ultimately converted to vinyl groups). Particularly when the process using mixed Pd/Pt catalyst is used on a para-acyl pyridine of Formula (2), i.e., when $A_4$ is acyl, one or a combination of % D5 and % D6 vinylpyridine compounds of Formula (1) can be produced in an amount of at least or above 50, 60, 65, 70, 80, 85, 90, or 95 mol %, particularly with $A_2$ and/or $A_6$ as deuterium atoms in a predominant amount (with the $A_4$ acyl group ultimately converted to a vinyl group).

In a second particular set of embodiments, at least or above 50, 60, 65, 70, 80, 85, 90, or 95 mol % of the compounds of Formula (1) has one of $A_2$, $A_3$, $A_4$, $A_5$, and $A_6$ as a vinyl group of the Formula (1-a) and two of $A_2$, $A_3$, $A_4$, $A_5$, and $A_6$ as deuterium atoms. In particular embodiments for achieving this, a Pd catalyst in the absence of Pt is used in step (i). The Pd catalyst can be any of the Pd catalysts described above. Particularly when the process using a Pd, Pt, or mixed Pd/Pt catalyst is used on a para-acyl pyridine of Formula (2), i.e., when $A_4$ is acyl, a % D5 vinylpyridine compound of Formula (1) can be produced in an amount of at least or above 50, 60, 65, 70, 80, 85, 90, or 95 mol %, particularly with $A_2$ and/or $A_6$ as deuterium atoms in a predominant amount (with the $A_4$ acyl group ultimately converted to a vinyl group).

In a third particular set of embodiments, at least or above 50, 60, 65, 70, 80, 85, 90, or 95 mol % of the compounds of Formula (1) has one of $A_2$, $A_3$, $A_4$, $A_5$, and $A_6$ as a vinyl group of the Formula (1-a) and the remainder of $A_2$, $A_3$, $A_4$, $A_5$, and $A_6$ as hydrogen atoms. In particular embodiments for achieving this, an Ir, Ni, or Pt metal-ligand complex is used as a catalyst in step (i). These metal-ligand catalysts can be any of such catalysts described above. In particular embodiments, the metal-ligand complex is selected from $[Cp*IrCl_2]_2$, $NiCp(PPh_3)Cl$, and $Pt(acac)_2$.

In a fourth particular set of embodiments, at least or above 50, 60, 65, 70, 80, 85, 90, or 95 mol % of the compounds of Formula (1) has one of $A_2$, $A_3$, $A_4$, $A_5$, and $A_6$ as a vinyl group of the Formula (1-a) and the remainder of $A_2$, $A_3$, $A_4$, $A_5$, and $A_6$ as deuterium atoms. In particular embodiments for achieving this, step (i) is conducted at a temperature of at least or above 100° C., 110° C., 120° C., 130° C., 140° C., 150° C., 160° C., 170° C., 180° C., 190° C., or 200° C., and at a pressure above 1 atm, such as a pressure of at least or above 2, 3, 4, 5, 10, 12, 15, 20, 30, 40, 50, 60, 70, 80, 90, or 100 atm, and below the critical temperature and pressure of water. In particular embodiments, the catalyst used in step (i) is selected from Pd, Pt, or a mixed Pd/Pt catalyst, as described above.

The invention is also directed to the polymerization of any of the above deuterated vinylpyridine compounds according to Formula (1) in the preparation of a polyvinylpyridine polymer and co-polymers. Methods for the preparation of polyvinylpyridine polymers from vinylpyridine monomers are well established, and all such methods are considered herein. Some of the methods for polymerizing vinylpyridines include, for example, free radical polymerization (FRP), anionic polymerization (AP), and controlled radical polymerization (CRP). Some more specific types of CRP include, for example, atom transfer radical polymerization (ATRP), degenerative transfer, reversible fragmentation chain transfer, and nitroxide-mediated polymerization. For the synthesis of a copolymer of vinylpyridine, the comonomer may be any suitable vinylic compound, such as, for example, styrene, acrylamide, acrylic acid, an acrylate ester, methacrylic acid, a methacrylate ester, acrylonitrile, or butadiene, or a combination thereof. The resulting polyvinylpyridines can be directed to any of a variety of applications, including as conductive polymers (e.g., as produced from polyvinylpyridine and iodine), battery cathode materials, photographic materials, textiles, dispersion media, and ion exchange materials.

Examples have been set forth below for the purpose of illustration and to describe certain specific embodiments of the invention. However, the scope of this invention is not to be in any way limited by the examples set forth herein.

EXAMPLE 1

Conversion of Acetylpyridines to Deuterated Acetylpyridines

Exemplary Procedure

In a sealed pressure tube, the acetylpyridine compound (100 mg), catalyst (10 mg) and $D_2O$ (7.0 mL) were combined. After two vacuum/$H_2$ cycles to replace air with $H_2$ gas, the mixture was stirred and heated at 180° C. for 24 hours. After the solution was cooled to room temperature (i.e., approximately 20-30° C.), the mixture was filtered through Celite® and washed with dichloromethane, i.e., methylene chloride (10 mL). The organic layer was isolated and dried over anhydrous $Na_2SO_4$. The solvent was removed by rotary evaporation, and the product was analyzed by GC/MS and NMR analysis.

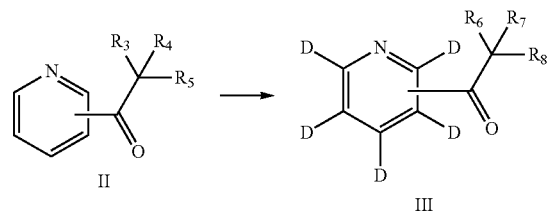

For the above reaction, where $R_3=R_4=R_5=H$, and $R_6=R_7=R_8=D$, a metal catalyst is used to effect the deuteration in deuterium oxide ($D_2O$) media. The effectiveness of the deuteration varies with the identity of the metal catalyst and the position of the carbonyl substituent group on the pyridine nucleus (that is, 2- or ortho-, 3- or meta-, and 4- or para-). The screening procedure above was used to identify which types of metal catalysts might be suitable for effecting this conversion.

Screening Results

Results showing the extent of deuteration by GC/MS as a function of metal catalyst for 2-acetylpyridine are shown in Table 1, below:

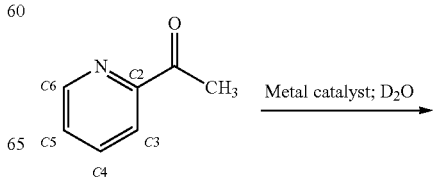

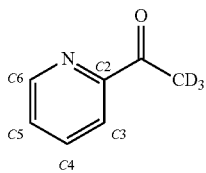

The catalysts [Cp*IrCl$_2$]$_2$ (where Cp* is pentamethylcycopentadienyl), NiCp(PPh$_3$)Cl (where Cp is cyclopentadienyl), and Pt(II) acetyl acetonate ("Pt(acac)$_2$"), at least under the conditions tested, were all surprisingly largely ineffective for H-D exchange on the pyridine nucleus, with the bulk of the H-D exchange taking place on the CH$_3$ group of the acetyl moiety. Thus, the foregoing three metal complexes can be particularly suited for the selective deuteration of the vinyl

TABLE 1

Extent of deuteration of 2-acetylpyridine as a function of catalyst, as determined by GC/MS

| Catalyst | % D1 | % D2 | % D3 | % D4 | % D5 | % D6 | % D7 | Which pyr carbons deuterated, as determined by $^{13}$C NMR |
|---|---|---|---|---|---|---|---|---|
| 5% Pt/C | ND* | 0.4 | 16.2 | 37.8 | 33.0 | 11.5 | 1.1 | No C3, C4, C5 slight; C6 partial |
| 10% Pd/C | ND | ND | 6.5 | 46.6 | 35.9 | 10.0 | 1.0 | Same as above |
| 1:1 5% Pt/C:10% Pd/C | ND | ND | ND | 5.5 | 30.8 | 58.6 | 5.1 | C3 slight, C4, C5 ca 70%; C6 >95% |
| [Cp * IrCl$_2$]$_2$ | ND | 1.6 | 89.9 | 7.8 | 0.7 | ND | ND | No C3, C4, C5; trace C6 |
| NiCp(PPh$_3$)Cl | ND | 2.7 | 86.6 | 9.8 | 0.9 | ND | ND | Same as above |
| Pt(acac)$_2$ | ND | 2.1 | 89.8 | 8.1 | ND | ND | ND | Same as above |

*ND = none detected.
Note, in all cases the —CH$_3$ group was nearly completely converted to —CD$_3$;
additional deuteration involves substitution of the aromatic pyridine —H with-D, at carbon positions 3, 4, 5, or 6.

From Table 1, above, it can be seen that with regard to deuteration of 2-acetylpyridine, zero-valent Pt (5 wt % loading) and Pd (10 wt % loading) on activated carbon are each somewhat effective, with most of the product being a mixture of D3, D4 and D5 incorporation. In all cases, the D3 incorporation reflects the exchange of the three protons on the acetyl methyl with deuterons; these protons are more labile than the aromatic protons and are more easily exchangeable. Synergism was observed in the aromatic H-D exchange when a 1:1 mixture of Pt and Pd was employed as the catalyst system, with nearly complete D-exchange of all the aromatic H's. The aromatic H at the 3-position, ortho to the acetyl moiety, was the least deuterated, likely due to steric congestion.

group in vinyl pyridine, leaving the pyridine moiety non-deuterated. Without being bound by any theory, the foregoing result may be due to the chemical environment of the metals in these complexes, which may render the metals incapable of forming a pi-arene type structure that may be necessary to activate the aromatic (in this case, pyridine) hydrogen atoms. Another possibility is that the pyridine nitrogen may interact with some of these catalysts by, for example, forming a complex with them.

Results showing the extent of deuteration by GC/MS as a function of metal catalyst for 4-acetylpyridine are shown in Table 2, below:

TABLE 2

Extent of deuteration of 4-acetylpyridine as a function of catalyst, as determined by GC/MS, and $^{13}$C NMR

| Catalyst | % D1 | % D2 | % D3 | % D4 | % D5 | % D6 | % D7 | Which pyr carbons deuterated, as determined by $^{13}$C NMR |
|---|---|---|---|---|---|---|---|---|
| 5% Pt/C | ND | 0.4 | 20.0 | 42.2 | 34.4 | 2.8 | 0.2 | C2 and C6 ca. 45%; C3, C5 trace |
| 10% Pd/C | ND | ND | ND | 3.5 | 87.2 | 8.4 | 0.9 | C2 and C6 mostly; C3, C5 trace |
| 1:1 5% Pt/C:10% Pd/C | ND | ND | ND | 4.4 | 87.2 | 7.7 | 0.6 | Same as above |
| [Cp*IrCl$_2$]$_2$ | ND | 1.7 | 83.6 | 13.1 | 1.5 | ND | ND | No C3, C5; trace C2, C6 |
| NiCp(PPh$_3$)Cl | ND | 2.7 | 88.5 | 8.8 | ND | ND | ND | Same as above |
| Pt(acac)$_2$ | ND | 2.2 | 87.1 | 9.6 | 1.1 | ND | ND | Same as above |

*ND = none detected.
Note, in all cases the —CH$_3$ group was nearly completely converted to —CD$_3$;
additional deuteration involves substitution of the aromatic pyridine —H with-D, at carbon positions 2, 3, 5, or 6.

Interestingly, when the same catalysts were used with 4-acetylpyridine (Table 2 above), there was more D5 product produced using Pd alone as compared to 2-acetylpyridine (likely due to equivalent positions C2 and C6 being equally deuterated), but no synergism was observed using the Pt+Pd mixture, the result being largely the same as Pd alone.

In subsequent steps, the deuterated acetyl group is converted first to a deuterated alcohol, and then finally to a deuterated vinyl group, to afford the deuterated vinylpyridines that are the subject of this invention. Depending on what types of catalysts and conditions are employed to deuterate the acetylpyridines, it is possible to produce deuterated vinylpyridines in which the vinyl group is fully deuterated, but the degree of deuteration of the pyridine ring can vary from fully-deuterated to non-deuterated.

For example, for 4-vinylpyridine, using the 10 wt % Pd/C catalyst system to obtain deuteration at the pyridine ring 2- and 6-positions can afford a 4-vinylpyridine-$d_5$ as shown:

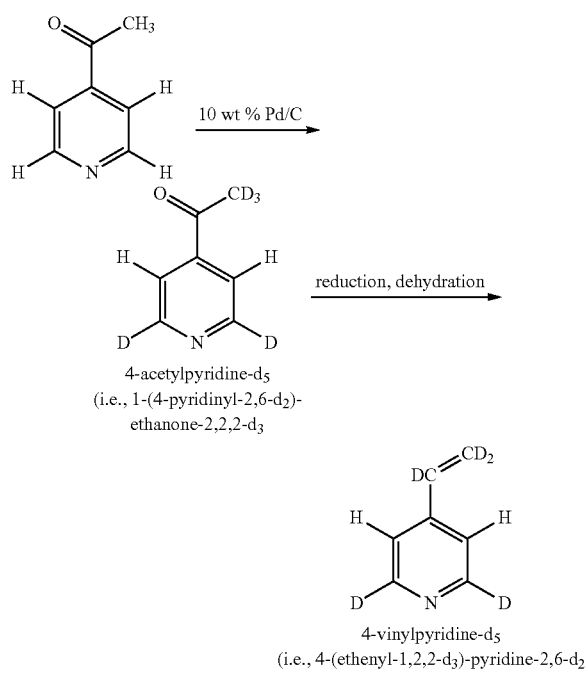

Such a material might be particularly useful for poly(4-vinylpyridines) wherein a lower degree of deuteration is desired at specific sites (here the 3- and 5-pyridine ring positions), both for NMR studies and for achieving a lower neutron scattering length density (SLD), that might be required for certain types of neutron scattering experiments, as compared with a fully deuterated vinylpyridine.

Similarly, if NiCp(PPh$_3$)Cl, which affords deuteration at mostly just the acetyl methyl but not the pyridine ring, is used as the catalyst, a 4-vinylpyridine-$d_3$ can be obtained in which only the vinyl group is deuterated:

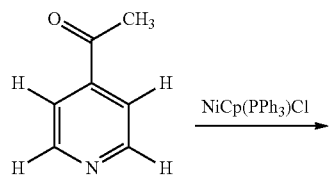

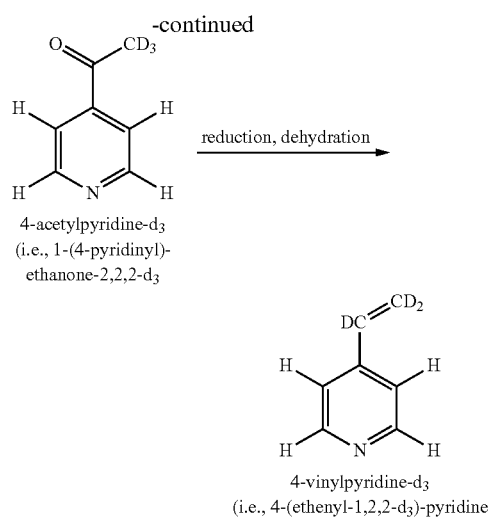

The vinyl group derived from the deuterated acetyl group in 1-(4-pyridinyl)-ethanone-2,2,2-$d_3$ produced using the NiCp(PPh$_3$)Cl catalyst is advantageously nearly completely deuterated. This monomer could be useful for preparing poly (4-vinylpyridines) wherein only the polymer backbone is deuterated, and the pyridine ring is essentially fully hydrogenated. This type of polymer could be useful for obtaining a different level of contrast in neutron scattering experiments, as well as a lower SLD.

Moreover, although the examples are provided for 2-acetylpyridine and 4-acetylpyridine, the same methodology can be employed for 3-acetylpyridine, and hence the invention is not limited to deuterated 2-vinyl and 4-vinylpyridines, but also includes deuterated 3-vinylpyridine derived from deuterated 3-acetylpyridine.

EXAMPLE 2

Procedures to Enhance Deuteration at Positions Ortho to the Acyl Group

It has herein been surprisingly found that, when the reaction using the mixed Pd/Pt catalyst is conducted in a Parr Reactor at a pressure greater than 1 atm, more extensive deuteration (e.g., up to 85% D) of the positions ortho to the acyl group becomes possible, affording the acetylpyridines that are nearly all D7, as further described in synthetic procedures below.

2-acetylpyridine-$d_7$

In order to explore preparative scale synthesis, a 1200 mL Parr reactor was used. In a typical procedure, 2-acetylpyridine (23.2 g, 192 mmol) was charged into a 1200 mL Parr reactor and then 2.31 grams of Pd (10 wt % on activated carbon) and 4.67 grams of Pt (5 wt % on activated carbon), followed by 700 grams of D$_2$O (98 D%). The reactor was purged with nitrogen for 15 minutes and then bubbled with hydrogen for three minutes. After closing all outlets, the reactor was heated to 180° C. while stirring. It took about 45 minutes to reach this temperature, and the final pressure was around 140-160 psi. The reaction was held under this condition (180° C. and ~150 psi) for 48 to 60 hours. After allowing the reactor and contents to cool to room temperature, and after carefully venting the system, the reaction mixture was filtered through Celite® to remove the catalysts. The Celite® was washed with diethyl ether (30 mL×3) and the filtrate was extracted with ether 200 mL×3. The combined organic layer was dried over anhydrous $Na_2SO_4$. The product was distilled and 14.6 grams was obtained. GC/MS characterized that D7 is ~85%, indicating a mass-adjusted yield of 115 mmol (60%).

4-acetylpyridine-$d_7$

In a manner similar to that described for 2-acetylpyridine, above, 4-acetylpyridine (21.3 g, 176 mmol) was charged into a 1200 mL Parr reactor and then 2.17 grams of Pd (10 wt % on activated carbon) and 4.28 grams of Pt (5 wt % on activated carbon), followed by 680 grams of $D_2O$ (98 D%). The reactor was purged with nitrogen for 15 minutes and then bubbled with hydrogen for three minutes. After closing all outlets, the reactor was heated to 180° C. while stirring. It took about 45 minutes to reach this temperature, and the final pressure was around 140-160 psi. The reaction was held under this condition (180° C. and ~150 psi) for 48 to 60 hours. After allowing the reactor and contents to cool to room temperature, and after carefully venting the system, the reaction mixture was filtered through Celite® to remove the catalysts. The Celite® was washed with diethyl ether (30 mL×3) and the filtrate was extracted with ether 200 mL×3. The combined organic layer was dried over anhydrous $Na_2SO_4$. The product was distilled, and 12.5 grams was obtained. GC/MS characterized that D7 is ~88%, indicating a mass-adjusted yield of 98 mmol (56%).

EXAMPLE 3

Preparation of 1-(pyridin-2-yl)ethanol-$d_9$ from 2-acetylpyridine-$d_7$

Under an argon atmosphere, 2-acetylpyridine-$d_7$ from Example 2 (0.82 g, 6.8 mmol), $NaBD_4$ (0.25 g, 6.9 mmol), and deuterated boric acid (0.44 g, 6.8 mmol) were combined together in a 30-mL heavy wall high density polyethylene screw cap vial, containing ca. 10 mL of ceramic beads (2 mm diameter) designed for ball milling. The cap was screwed tight and sealed with electrical tape, and the vial agitated using a SPEX 8000M Mixer/Mill® in a fume hood (Caution: reaction is exothermic and should be performed only in an approved fume hood behind a barrier) for about five minutes at 200 Hz during which the bottle vials became warm. The bottle was opened in the fume hood, and 5 mL of 1N DCl in $D_2O$ was slowly added to quench the reaction. The mixture was extracted with dichloromethane. The organic layer was dried over anhydrous magnesium sulfate, and the volatiles removed in vacuo to afford 0.64 g 1-(pyridin-2-yl)ethanol-$d_9$ in 78% isolated yield at >99% purity by GC/MS.

EXAMPLE 4

Preparation of 1-(pyridin-4-yl)ethanol-$d_9$ from 4-acetylpyridine-$d_7$

In a manner similar to that described for Example 3 above, under an argon atmosphere, 4-acetylpyridine-$d_7$ from Example 2 (0.60 g, 5 mmol), $NaBD_4$ (0.19 g, 5 mmol), and deuterated boric acid (0.31 g, 5 mmol) were combined together in a 30 mL heavy wall high density polyethylene screw cap vial, containing ca. 10 mL of ceramic beads (2 mm diameter) designed for ball milling. The cap was screwed tight and sealed with electrical tape, and the vial agitated using a SPEX 8000M Mixer/Mill® in a fume hood (Caution: reaction is exothermic and should be performed only in an approved fume hood behind a barrier) for five minutes at 200 Hz during which the bottle vials became warm. The bottle was opened in the fume hood, and 5 mL of 1 N DCl in $D_2O$ was slowly added to quench the reaction. The mixture was extracted with dichloromethane. The organic layer was dried over anhydrous magnesium sulfate, and the volatiles removed in vacuo to afford 1-(pyridin-4-yl)ethanol-$d_9$ in 73% isolated yield at >99% purity by GC/MS.

EXAMPLE 5

Preparation of 2-vinylpyridine-$d_7$ from 1-(pyridin-2-yl)ethanol-$d_9$

In a typical reaction, 5.5 g (42 mmol) of 1-(pyridin-2-yl) ethanol-$d_9$ from Example 3 in 50 mL dichloromethane containing about 10 mg of butylated hydroxy toluene (BHT, as inhibitor) was charged into a 250-mL two-neck round bottom flask containing a stirbar, and equipped with a pressure-equalizing addition funnel that contained 6.3 grams (65 mmol) of methanesulfonic acid dissolved in 10 mL dichloromethane. The methanesulfonic acid solution was added dropwise to the stirred reaction mixture at room temperature over the course of 20 minutes, then the addition funnel was replaced with a condenser and the reaction mixture was refluxed for four hours. Analysis of the reaction mixture during this time using thin layer chromatography (TLC) indicated that the starting materials were consumed after 3.5 hours. The reaction was allowed to cool to room temperature, and then 80 mL of dichloromethane was added. NaOH (1.0 N) was added dropwise to neutralize the solution and to bring the pH up to about 10. The aqueous layer was then extracted with dichloromethane (3×30 mL) and the combined organic layers were dried over anhydrous $Na_2SO_4$, filtered, and concentrated under vacuum at room temperature to yield 4.4 g (39 mmol, 93% yield) of crude 2-vinylpyridine-$d_7$. The crude material was purified by bulb-to-bulb vacuum distillation, to afford 3.0 g (63%) of analytically pure 2-vinylpyridine-$d_7$.

EXAMPLE 6

Preparation of 4-vinylpyridine-$d_7$ from 1-(pyridin-4-yl)ethanol-$d_9$

In a typical reaction, 4.7 g (36 mmol) of 1-(pyridin-4-yl) ethanol-$d_9$ from Example 4 in 50 mL dichloromethane containing about 20 mg of BHT (as inhibitor) was charged into a 250-mL two-neck round bottom flask containing a stirbar, and equipped with a pressure-equalizing addition funnel that contained 6.3 grams (65 mmol) of methanesulfonic acid dissolved in 10 mL of dichloromethane. The methanesulfonic acid solution was added dropwise to the stirred reaction mixture at room temperature over the course of 25 minutes, then the addition funnel was replaced with a condenser and the reaction mixture was refluxed for five hours. The reaction was allowed to cool to room temperature, and then 50 mL of dichloromethane was added. NaOH (1.0 N) was added dropwise to neutralize the solution and to bring the pH up to about 10. The aqueous layer was then extracted with dichloromethane (3×30 mL) and the combined organic layers dried over anhydrous $Na_2SO_4$, filtered, and concentrated under vacuum at room temperature to yield 3.42 g (30 mmol, 83% yield) of crude 4-vinylpyridine-$d_7$. Further purification was achieved by distillation over $CaH_2$.

EXAMPLE 7

Anionic Polymerization of 2-vinylpyridine-$d_7$

The 3-g quantity of 2-vinylpyridine-$d_7$ (2-VP) from Example 5 was stirred over $Al(C_4H_9)_3$ for about 3 hours, and degassed three times. Then about 2.4 mL of the 2-vinylpyridine-$d_7$ was distilled into a graduated ampoule under high vacuum. The ampoule containing the monomer was then connected via glass-blowing techniques to a sidearm connected to a custom-made 250-mL glass bulb apparatus (with stir bar) connected to a high vacuum line. The ampoule contained a break-seal. The glass bulb contained a second sidearm, to which three separate ampoules with break seals were attached in a row. One ampoule contained n-BuLi (6.0 mL of 0.037 M in hexanes), another contained a solution of 0.17 mL 1,1-diphenylethylene (DPE) in 5.0 mL benzene, and the last ampoule contained degassed methanol. The apparatus was then pinhole/leak tested, and then ~40 mL of tetrahydrofuran (THF, dried over Na/K alloy) was transferred to the interior of the bulb by in-line distillation through the vacuum line. The n-BuLi and DPE solutions were then admitted to the bulb by breaking the seals on their respective ampoules. These solutions were allowed to react for 30 minutes at room temperature. The solution was red in color, indicating the presence of active anionic initiator. The solution in the bulb was then cooled down to −78° C. The seal on the 2-VP ampoule was then broken to introduce the monomer to the solution. The mixture was stirred for ~2 hours at −78° C., during which the 2-VP polymerized. The polymerization was terminated by breaking the seal on the degassed methanol ampoule, and admitting the methanol to the reaction mixture. The reaction was then allowed to warm up to room temperature, and the seal of the bulb broken. The reaction mixture was then poured into ~200 mL hexanes to precipitate the 2-VP polymer. The polymer was collected by filtration, and the white solid dried under vacuum until a constant weight was obtained (1.93 g). The polymer was analyzed by Gel Permeation Chromatography (GPC) using THF containing 3 vol % triethylamine (TEA) as the mobile phase. The results indicated that the molecular weight (MW) of the polymer is about 13.9 kg/mol with a polydispersity index (PDI) of 1.26.

While there have been shown and described what are at present considered the preferred embodiments of the invention, those skilled in the art may make various changes and modifications which remain within the scope of the invention defined by the appended claims.

What is claimed is:

1. A method for synthesizing deuterated vinylpyridine compounds of the formula:

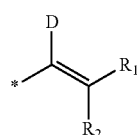

(1)

wherein one of $A_2, A_3, A_4, A_5,$ and $A_6$ is a vinyl group of the formula:

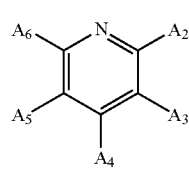

(1-a)

wherein $R_1$ and $R_2$ are each independently either a deuterium atom or a perdeuterated alkyl group containing one to six carbon atoms;

the remainder of $A_2, A_3, A_4, A_5,$ and $A_6$ are independently selected from hydrogen and deuterium atoms; and the method comprising the steps of:

(i) deuterating a compound of Formula (2) to a compound of Formula (3) by the following reaction pathway conducted in the presence of a metal catalyst and $D_2O$, wherein the metal catalyst is active for hydrogen exchange in water:

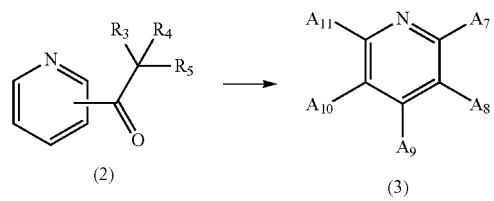

$R_3, R_4,$ and $R_5$ are independently selected from hydrogen atom and alkyl groups containing one to six carbon atoms, provided that at least one of $R_3, R_4,$ and $R_5$ is a hydrogen atom;

one of $A_7, A_8, A_9, A_{10},$ and $A_{11}$ is an acyl group of the formula:

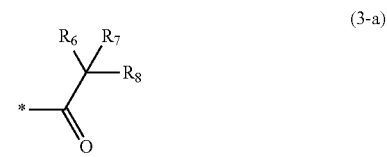

(3-a)

wherein $R_6, R_7,$ and $R_8$ are independently selected from deuterium atom and perdeuteroalkyl groups containing one to six carbon atoms, provided that at least one of $R_6, R_7,$ and $R_8$ is a deuterium atom;

(ii) reducing the compound of Formula (3) with a deuterated reducing agent to convert the acyl group of Formula (3-a) to an alcohol group of the Formula (3-b):

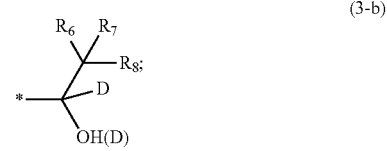

(3-b)

and (iii) dehydrating the compound produced in step (ii) with a dehydrating agent to afford the vinylpyridine compound of Formula (1).

2. The method of claim 1, wherein $R_1, R_2, R_6, R_7,$ and $R_8$ are deuterium atoms, and $R_3, R_4,$ and $R_5$ are hydrogen atoms.

3. The method of claim 1, wherein the metal of said metal catalyst in step (i) is selected from Pd, Pt, Ni, Ru, Rh, Ir, and combinations thereof.

4. The method of claim 1, wherein the metal of said metal catalyst in step (i) is selected from Pd, Pt, and mixtures thereof.

5. The method of claim 1, wherein said metal catalyst in step (i) is comprised of a catalytically active metal on a carbon support.

6. The method of claim 1, wherein step (i) is conducted at a temperature of at least 50° C. and below the critical temperature of water.

7. The method of claim 1, wherein step (i) is conducted at a temperature above 100° C. and below the critical temperature of water.

8. The method of claim 1, wherein step (i) is conducted at a temperature above 150° C. and below the critical temperature of water.

9. The method of claim 1, wherein step (i) is conducted at a pressure above 1 atm and below the critical pressure of water.

10. The method of claim 1, wherein said deuterated reducing agent is selected from aluminum deteurides and borodeuterides.

11. The method of claim 1, wherein said dehydrating agent is comprised of aluminum oxide.

12. The method of claim 1, wherein at least 80 mol % of the compounds of Formula (1) has one of $A_2, A_3, A_4, A_5$, and $A_6$ as a vinyl group of the Formula (1-a) and two or three of $A_2, A_3, A_4, A_5$, and $A_6$ as deuterium atoms.

13. The method of claim 12, wherein the metal of the metal catalyst in step (i) is comprised of a mixture of Pd and Pt.

14. The method of claim 12, wherein said at least 80 mol % of the compounds of Formula (1) has $A_2$ or $A_6$ as a vinyl group of the Formula (1-a).

15. The method of claim 12, wherein said at least 80 mol % of the compounds of Formula (1) has $A_4$ as a vinyl group of the Formula (1-a).

16. The method of claim 1, wherein at least 80 mol % of the compounds of Formula (1) has one of $A_2, A_3, A_4, A_5$, and $A_6$ as a vinyl group of the Formula (1-a) and two of $A_2, A_3, A_4, A_5$, and $A_6$ as deuterium atoms.

17. The method of claim 16, wherein the metal of the metal catalyst in step (i) is comprised of Pd in the absence of Pt.

18. The method of claim 16, wherein the metal of the metal catalyst in step (i) is comprised of a mixture of Pd and Pt.

19. The method of claim 16, wherein the compound of Formula (1) has $A_4$ as a vinyl group of the Formula (1-a).

20. The method of claim 1, wherein at least 80 mol % of the compounds of Formula (1) has one of $A_2, A_3, A_4, A_5$, and $A_6$ as a vinyl group of the Formula (1-a) and the remainder of $A_2, A_3, A_4, A_5$, and $A_6$ as hydrogen atoms.

21. The method of claim 20, wherein the metal catalyst in step (i) is selected from [Cp*IrCl$_2$]$_2$, NiCp(PPh$_3$)Cl, and Pt(acac)$_2$, wherein Cp* represents a pentamethylcyclopentadienyl group, Cp represents a cyclopentadienyl group, PPh$_3$ represents a triphenylphosphine group, and acac represents an acetylacetonate group.

22. The method of claim 1, wherein at least 80 mol % of the compounds of Formula (1) has one of $A_2, A_3, A_4, A_5$, and $A_6$ as a vinyl group of the Formula (1-a) and the remainder of $A_2, A_3, A_4, A_5$, and $A_6$ as deuterium atoms.

23. The method of claim 22, wherein the metal of the metal catalyst in step (i) is comprised of a mixture of Pd and Pt.

24. The method of claim 22, wherein step (i) is conducted at a temperature above 100° C. and at a pressure above 1 atm, and below the critical temperature and pressure of water.

25. The method of claim 22, wherein step (i) is conducted at a temperature above 100° C. and at a pressure of at least 10 atm, and below the critical temperature and pressure of water.

26. The method of claim 22, wherein step (i) is conducted at a temperature above 150° C. and at a pressure above 1 atm, and below the critical temperature and pressure of water.

27. The method of claim 22, wherein step (i) is conducted at a temperature above 150° C. and at a pressure of at least 10 atm, and below the critical temperature and pressure of water.

28. The method of claim 1, further comprising an additional step wherein the vinylpyridine compound of Formula (1) is reacted with a Bronsted acid or alkylating agent to produce a charged pyridinium species wherein the nitrogen atom of the pyridine ring is bound to a hydrogen atom, deuterium atom, or an alkyl group optionally substituted with one or more deuterium atoms, wherein said Bronsted acid is optionally deuterated, and said alkylating agent contains an alkyl group optionally substituted with one or more deuterium atoms.

\* \* \* \* \*